US012782275B2

(12) United States Patent
Takagi et al.

(10) Patent No.: US 12,782,275 B2
(45) Date of Patent: Nov. 3, 2026

(54) GAS SENSOR AND SENSING METHOD

(71) Applicant: Asahi Kasei Microdevices Corporation, Tokyo (JP)

(72) Inventors: Yuta Takagi, Tokyo (JP); Naoya Ugomori, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 142 days.

(21) Appl. No.: 18/780,537

(22) Filed: Jul. 23, 2024

(65) Prior Publication Data

US 2025/0035545 A1 Jan. 30, 2025

(30) Foreign Application Priority Data

Jul. 27, 2023 (JP) ................................ 2023-122833
Jun. 24, 2024 (JP) ................................ 2024-101205

(51) Int. Cl.
*G01N 21/3504* (2014.01)
*G01N 33/497* (2006.01)

(52) U.S. Cl.
CPC ....... *G01N 21/3504* (2013.01); *G01N 33/497* (2013.01)

(58) Field of Classification Search
CPC .. G01N 21/3504; G01N 33/497; G01N 21/01; G01N 21/27; G01N 21/31; G01N 21/64; G01N 21/17
See application file for complete search history.

(56) References Cited

U.S. PATENT DOCUMENTS 5,570,697 A 11/1996 Walker
6,081,742 A 6/2000 Amano
2006/0139647 A1* 6/2006 Tice ...................... G01N 21/15 356/437
2010/0249631 A1 9/2010 Aoki
2012/0055726 A1 3/2012 Hannon
2014/0361172 A1* 12/2014 Little, III ............ G01N 21/359 250/339.06
2016/0231244 A1* 8/2016 Camargo ........... G01N 21/0303
2020/0141914 A1 5/2020 Mizuuchi
2021/0396658 A1 12/2021 Denda

FOREIGN PATENT DOCUMENTS

JP 2003232732 A 8/2003
JP 2019174152 A 10/2019

* cited by examiner

*Primary Examiner* — Courtney D Thomas

(57) ABSTRACT

Provided is a gas sensor that senses gas to be sensed, comprising a light emitting unit that radiates light; a first light receiving unit that receive at least a part of the light that passed through the gas to be sensed, and outputs a first light reception signal according to a light reception result; a second light receiving unit that receives at least a part of the light that did not pass through the gas to be sensed, and outputs a second light reception signal according to a light reception result; and an operating unit that senses that condensation has occurred in a light path from the light emitting unit to the first light receiving unit based on the first light reception signal and the second light reception signal.

18 Claims, 15 Drawing Sheets

GAS SENSOR AND SENSING METHOD

The contents of the following patent application(s) are incorporated herein by reference:

NO. 2023-122833 filed in JP on Jul. 27, 2023

NO. 2024-101205 filed in JP on Jun. 24, 2024

BACKGROUND

1. Technical Field

The present invention relates to a gas sensor and a sensing method.

2. Related Art

Conventionally, a measurement apparatus for measuring a concentration of respiratory gas or a gas is known (see patent documents 1 to 3, for example). Patent Documents Patent Document 1: Japanese Patent No. 5351583

Patent Document 2: Japanese Patent Application Publication No. 2022-3321

Patent Document 3: Japanese Patent Application Publication No. 2019-174152

DESCRIPTION OF EXEMPLARY EMBODIMENTS

Hereinafter, the present invention will be described through embodiments of the invention, but the following embodiments do not limit the invention according to the claims. In addition, not all of the combinations of features described in the embodiments are essential to the solution of the invention. In the present specification, the same parts in each figure are denoted by the same signs and numerals, and the descriptions thereof may be omitted. In addition, for convenience of description, some configurations may not be illustrated.

In the present specification, technical matters may be described using orthogonal coordinate system of an X axis, a Y axis, and a Z axis. The orthogonal coordinate system merely specifies relative positions of components, and does not limit a particular direction. For example, the Z-axis direction is not limited to illustrating the height direction relative to the ground.

Figure 1:
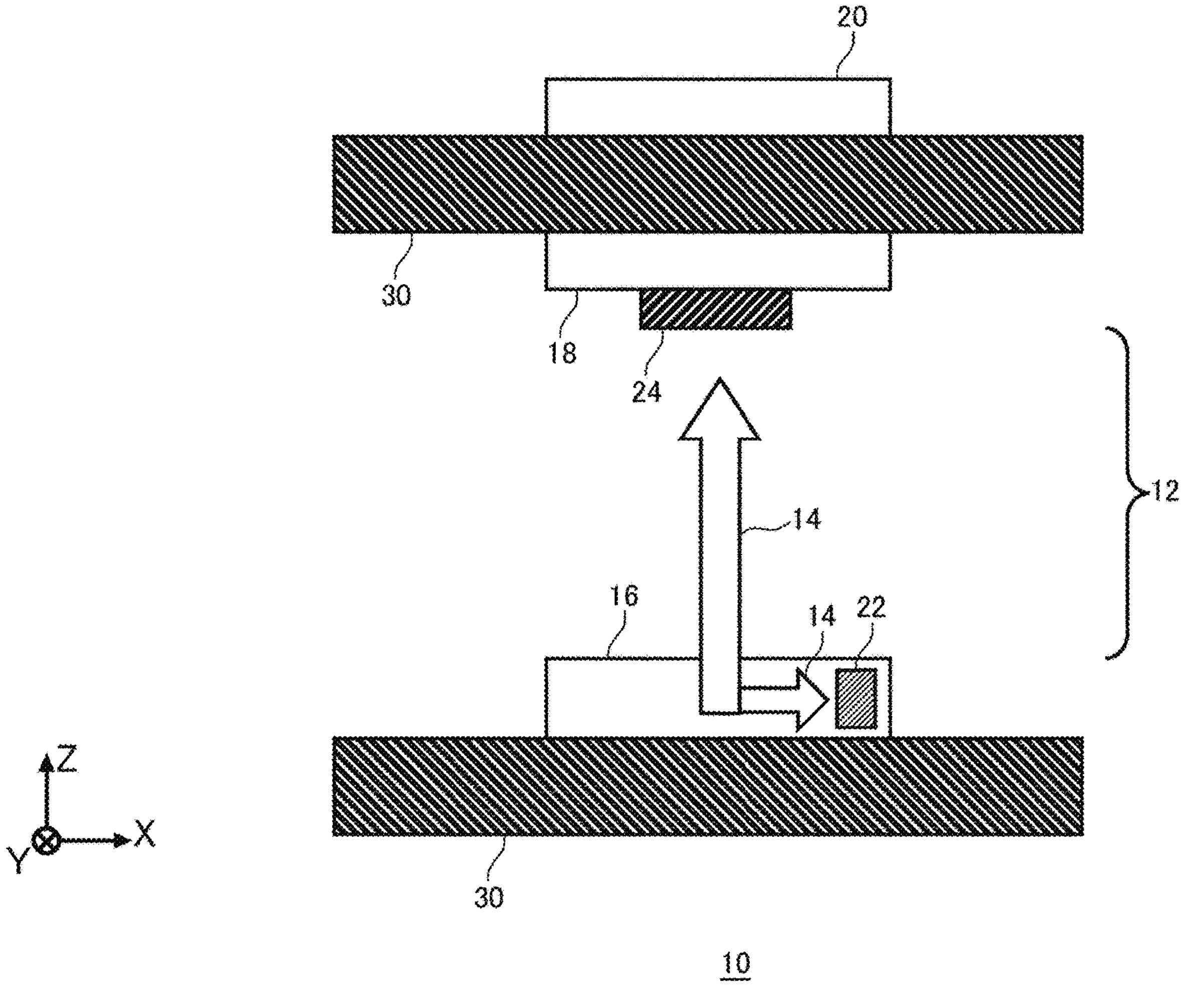
FIG. 1 illustrates a gas sensor 10 that senses a gas to be sensed.

FIG. 1 illustrates a gas sensor 10 that senses gas to be sensed. The gas sensor 10 includes a light emitting unit 16, a first light receiving unit 18, and an operating unit 20. The light emitting unit 16, the first light receiving unit 18, and the operating unit 20 may be attached to a support member 30. In the present example, the light emitting unit 16 is attached to one of the support members 30 facing each other, and the first light receiving unit 18 and the operating unit 20 are attached to the other. In the present example, description is made by defining a surface that is parallel to a main surface of the support member 30 as the XY plane, and defining a direction that is orthogonal to the main surface of the support member 30 as the Z-axis direction.

The gas sensor 10 is an optical gas sensor that uses a specific absorption wavelength that the component included in the gas to be sensed has. The light emitting unit 16 radiates light 14 toward a path 12 through which the gas to be sensed passes. The light emitting unit 16 is an LED, as an example. The wavelength of the light 14 may be appropriately selected according to the absorption wavelength of the gas to be sensed. A part of the light 14 passes through the path 12 and enters the first light receiving unit 18. A part of the light 14 enters a second light receiving unit 22 described below.

The first light receiving unit 18 receives at least a part of the light 14 that passed the gas to be sensed, and outputs a first light reception signal according to a light reception result to the operating unit 20. The first light receiving unit 18 is a photodiode, as an example.

The operating unit 20 performs operation on the first light reception signal. The operating unit 20 is an IC, as an example. Since the gas to be sensed absorbs the light 14, which causes the light-receiving amount in the absorption wavelength of the gas to be sensed to be decreased, the operating unit 20 can perform operation to obtain, from a value of the first light reception signal, a concentration of the gas to be sensed or a value according to the concentration.

Here, a specific example of an operation of first light amount information Φ1 related to light amount information absorbed by the gas to be sensed is illustrated, as an example of an operation performed on the first light reception signal. By defining the wavelength (μm) as λ, the intensity of the light, among the light 14 emitted from the light emitting unit 16, that reached the first light receiving unit 18 in a case where a sensing gas does not exist is represented by $\Phi 1(\lambda)$, and the responsivity of the first light receiving unit 18 is defined as $Ri_1(\lambda)$. The optical path length from the light emitting unit 16 to the first light receiving unit 18 is defined as L. In addition, the absorption light coefficient of the sensing gas is defined as $\mu(\lambda)$, and the concentration of the gas to be sensed is defined as c. Here, although $\Phi(\lambda)$ is a case where the sensing gas does not exist, it may be a case where some kind of a target gas of a reference concentration exists, or the like.

Expression 1

$$\phi 1 \propto \int \phi_1(\lambda) Ri_1(\lambda)\left(1 - e^{-c\mu(\lambda)L}\right) d\lambda \quad (1)$$

The first light amount information Φ1 changes according to the concentration c of the sensing gas. The higher the concentration of the sensing gas, the larger Φ1 becomes.

Here, Φ1 may be subjected to correction by temperature information. In this case, the gas sensor 10 may further include a thermometer, and the operating unit 20 may receive a temperature signal from said thermometer. Taking a term of temperature into consideration, Expression 1 can be expressed as the following Expression 2.

Expression 2

$$\phi 1 \propto \int \phi_1(\lambda, Temp) Ri_1(\lambda, Temp)\left(1 - e^{-c\mu(\lambda, Temp)L}\right) d\lambda \quad (2)$$

Here, defining the temperature corrected expression as f1, and a value obtained by subjecting tabExpression 2 to temperature correction as Φ1comp, it can be expressed as Expression 3 below.

Expression 3

$$\phi 1comp \propto f_1(Temp) \int \phi_1(\lambda, Temp) Ri_1(\lambda, Temp)\left(1 - e^{-c\mu(\lambda, Temp)L}\right) d\lambda \quad (3)$$

The first light amount information Φ1 of any of Expressions 1 to 3 may be used for sensing of the condensation described below. Sensing of the condensation may be performed by comparing the first light amount information Φ1 with a first set value A1. A threshold for the first set value A1 is decided by using the fact that further signal variation occurs in the absorption light amount expected by the gas sensing when condensation normally occurs. For example, in a case of a carbon dioxide sensor that is used for breath sensing sensor, the first set value A1 is decided based on the absorption light amount by a carbon dioxide concentration of 40000 ppm included in the breath. Normally, the carbon dioxide concentration included in the breath does not exceed about 40000 ppm. On the other hand, a signal variation that is equal to or greater than the variation in the absorption light amount by 40000 ppm of carbon dioxide may occur when condensation has occurred.

The gas sensor 10 may include the second light receiving unit 22. The second light receiving unit 22 may be built in in the light emitting unit 16. Configurations of the light emitting unit 16 and the second light receiving unit 22 will be described below. The second light receiving unit 22 receives the light 14, among the light 14 emitted by the light emitting unit 16, that did not pass through the path 12 through which the gas to be sensed passes, and outputs a second light reception signal according to the light reception result. The second light receiving unit 22 may receive at least a part of the light 14 that did not pass through the gas to be sensed. The second light reception signal may be output to the operating unit 20. The operating unit 20 may correct the first light reception signal by using a signal value of the second light reception signal. Correction may mean to divide a value of the first light reception signal by a value of the second light reception signal. By providing the second light receiving unit 22 and performing correction, the output variation duet to change in the light amount of the light emitting unit 16 and temperature can be corrected.

The operating unit 20 may correct the first light amount information by using the second light reception signal. Here, as an example of correction, a specific example of an operation of second light amount information Φ2 related to light amount information absorbed by the gas to be sensed is illustrated. By defining the wavelength (μm) as λ, the intensity of the light, among the light 14 emitted from the light emitting unit 16, that reached the first light receiving unit 18 in a case where a sensing gas does not exist is represented by $\Phi_1(\lambda)$, the intensity of the light that reached the second light receiving unit is represented by $\Phi_2(\lambda)$, the responsivity of the first light receiving unit 18 is defined as $Ri_1(\lambda)$ and the responsivity of the second light receiving unit 22 is defined as $Ri_2(\lambda)$. The optical path length from the light emitting unit 16 to the first light receiving unit 18 is defined as L. In addition, the absorption light coefficient of the sensing gas is defined as μ(λ), and the concentration of the gas to be sensed is defined as c. Here, although $\Phi_1(\lambda)$ is a case where the sensing gas does not exist, it may be a case where some kind of a target gas of a reference concentration exists, or the like. The second light amount information Φ2 can be obtained from Expression 4.

Expression 4

$$\phi 2 \propto \frac{\int \phi_1(\lambda) Ri_1(\lambda)\left(1 - e^{-c\mu(\lambda)L}\right) d\lambda}{\int \phi_2(\lambda) Ri_2(\lambda) d\lambda} \quad (4)$$

Here, the second light amount information Φ2 may be subjected to correction by temperature information. In this case, the gas sensor 10 may further include a thermometer, and the operating unit 20 may receive a temperature signal from said thermometer. Taking a term of temperature into consideration, Expression 4 can be expressed as the following Expression 5.

Expression 5

$$\phi 2 \propto \frac{\int \phi_1(\lambda, Temp) Ri_1(\lambda, Temp)\left(1 - e^{-c\mu(\lambda, Temp)L}\right) d\lambda}{\int \phi_2(\lambda, Temp) Ri_2(\lambda, Temp) d\lambda} \quad (5)$$

Here, defining the temperature corrected expression of a signal of the light reception sensor as f1, the temperature corrected expression of a signal of the second light receiving unit as f2, and a value obtained by subjecting Expression 5 to temperature correction as Φ2comp, it can be expressed as Expression 6 below.

Expression 6

$$\phi 2comp \propto \frac{t_1(Temp) \int \phi_1(\lambda, Temp) Ri_1(\lambda, Temp)\left(1 - e^{-c\mu(\lambda, Temp)L}\right) d\lambda}{f_2(Temp) \int \phi_2(\lambda, Temp) Ri_2(\lambda, Temp) d\lambda} \quad (6)$$

In addition, given that $Ri_1$ is corrected by $Ri_2$, the temperature corrected expression may be applied to the quotient of each sensor signal. In this case, the following Expression 7 will be used.

Expression 7

$$\phi 2comp \propto f(Temp) * \frac{\int \phi_1(\lambda, Temp)Ri_1(\lambda, Temp)\left(1 - e^{-c\mu(\lambda, Temp)L}\right)d\lambda}{\int \phi_2(\lambda, Temp)Ri_2(\lambda, Temp)d\lambda} \quad (7)$$

The gas sensor 10 may further include an optical filter 24 arranged between the light emitting unit 16 and the first light receiving unit 18. The optical filter 24 in the present example is provided on a surface of the first light receiving unit 18. The optical filter 24 restricts the wavelength of light 14 that enters the first light receiving unit 18. The optical filter 24 is a band-pass filter, as an example. When the transmission rate of the band-pass filter is defined as $T_{BPF}(\lambda)$, Expression 1 can be expressed as the following Expression 8.

Expression 8

$$\phi 1 \propto \int \phi_1(\lambda)Ri_1(\lambda)T_{BPF}(\lambda)\left(1 - e^{-c\mu(\lambda)L}\right)d\lambda \quad (8)$$

Generally, the responsivity of the first light receiving unit 18 is changed by being influenced by the temperature. In a responsivity curve where the horizontal axis indicates the wavelength of light and the vertical axis indicates the responsivity of the first light receiving unit 18, the influence of the temperature appears as a shift in a horizontal axis direction of the responsivity curve. On the other hand, the responsivity curve has a wavelength range in which most of the responsivity values are significantly flat. By causing only light with a wavelength in said wavelength range to enter the first light receiving unit 18 using the optical filter 24, the influence on the responsivity can be suppressed even when the temperature of the first light receiving unit 18 changes.

The type of the gas to be sensed is not restricted in particular, but as an example in the present specification, the gas to be sensed is described as breath. In the present specification, when the gas to be sensed is breath, although it is described that carbon dioxide included in breath absorbs the light 14, alcohol or the like may absorb the light 14. The gas sensor 10 that senses breath may be provided on a microphone apparatus, or may be provided on an apparatus to be worn on the head. The gas sensor 10 may be provided on a microphone part of a headphone.

Figure 2:
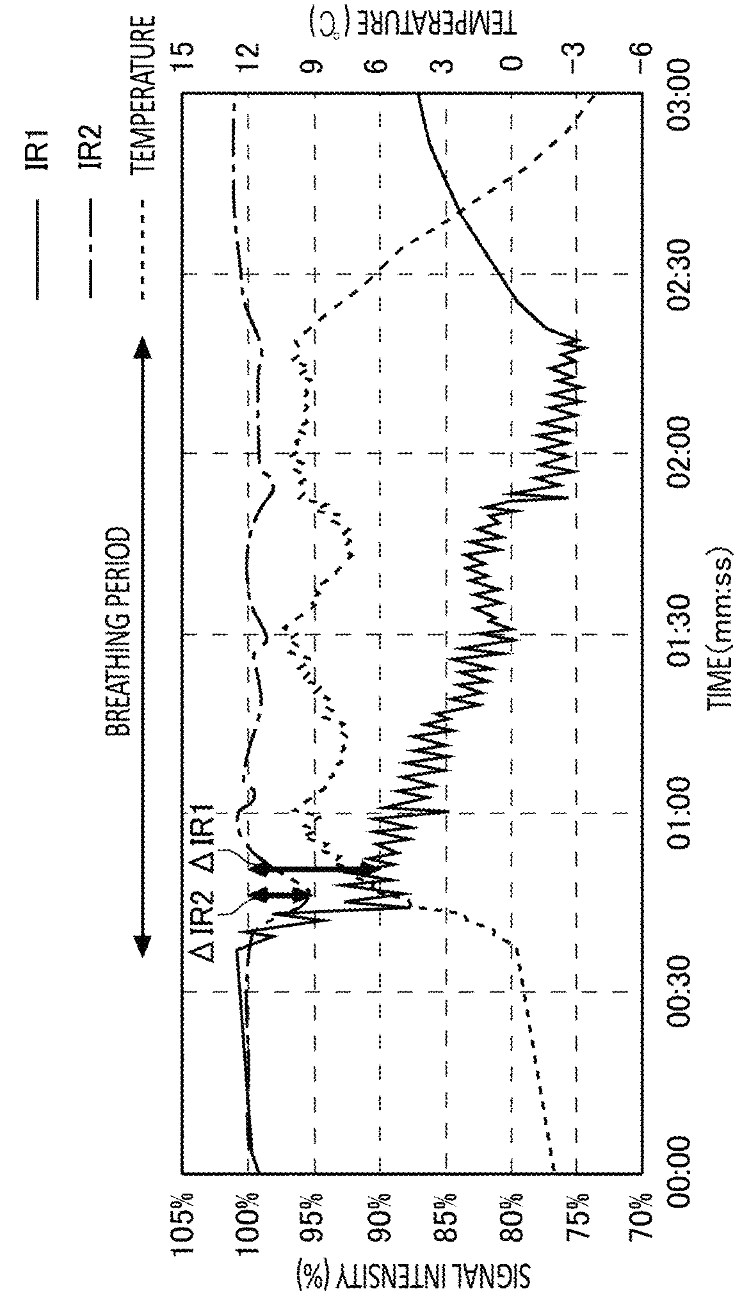
FIG. 2 illustrates a change in signal values when condensation has occurred in a light emitting unit 16 or a first light receiving unit 18.

FIG. 2 illustrates a change in signal values when condensation has occurred in the light emitting unit 16 or the first light receiving unit 18. In FIG. 2 and subsequent figures, the first light reception signal is represented as IR1, and the second light reception signal is represented as IR2. In FIG. 2, the horizontal axis represents the time, the vertical axis on the left-hand side represents the signal strength (%) of a value of the first light reception signal and the signal strength (%) of a value of the second light reception signal, and the vertical axis on the right-hand side represents the temperature. A reference for the signal strength may be a signal value when no breath exists. The signal strength in the present example is a value in which a value of each signal is represented by percentage, where the value of the each signal when no breath exists is normalized as 100% (reference value). The difference between the reference value and the signal strength is the variation rate. In the case of the present example, the following can be represented: the variation rate (%)=reference value (100%)−signal strength (%). The farther the signal strength becomes from 100%, the variation rate is increased and the variation from the reference value is larger. Note that, the reference value may be a value other than 100%. The solid lines in the figure represent the first light reception signal, the one-dot chain line in the figure represents the second light reception signal, and the dotted line in the figure represents the temperature of the gas sensor 10. In addition, the variation rate ΔIR1 of the first light reception signal and the variation rate ΔIR2 of the second light reception signal are shown in the figure. The operating unit 20 may calculate the variation rate ΔIR1 of the first light reception signal and the variation rate ΔIR2 of the second light reception signal. In the present specification, the value of the first light reception signal case may simply be referred to as the first light reception signal, and the value of the second light reception signal may simply be referred to as the second light reception signal. In addition, the operating unit 20 may use the signal value as is for the operation, or may use a value obtained by converting the signal value into a variation rate for the operation. The term "signal value" and the term "variation rate" may be used interchangeably.

In FIG. 2, breath is blown onto the gas sensor 10 that is cooled to about 0° C. Breathing is performed from 40 seconds to 2 minutes and 20 seconds in the figure, and the gas sensor 10 senses the breath during the above-described period. The above-described period is shown as the breathing period in the figure. The light-receiving amount by the first light receiving unit 18 is decreased due to absorption of carbon dioxide, the first light reception signal is decreased when breath is sensed. In addition, since breath is quickly spread in the air, the first light reception signal immediately increases (recovers) after the decrease. Minute variation in the first light reception signal at around 40 seconds to 2 minutes and 20 seconds in the figure corresponds to the breathing. One valley-like portion in the first light reception signal ratio corresponds to one breathing. In FIG. 2, breathing is performed approximately 40 times during the breathing period.

The second light reception signal represents a light reception result of the light 14 that did not pass through the path 12 through which the gas to be sensed passes. Therefore, no variation is observed in the value of the second light reception signal due to breathing. The temperature of the gas sensor 10 is increased from around 0° C. due to temperature of the breath after beginning of the breathing, and repeats increase and decrease while the breathing continues, and is gradually decreased after the breathing is over.

When the breath is sensed, condensation may occur in the gas sensor 10 due to moisture included in the breath. In FIG. 2, the breath is blown onto the gas sensor 10 at 0° C., and condensation is purposely caused to occur in the gas sensor 10.

When condensation has occurred in the light emitting unit 16 or the first light receiving unit 18 of the gas sensor 10, a part of the light 14 is bent to an unintended direction due to absorption, reflection or refraction caused by the condensation, thereby the first light reception signal is influenced. In FIG. 2, the first light reception signal is significantly reduced at around 40 seconds, and continues to be reduced during the subsequent breathing period. This reduction in the first light reception signal is considered to be influenced by condensation due to the breath.

When condensation occurs, the S/N ratio of the first light reception signal is reduced, which causes a false-positive rate to be increased. Note that, a case where condensation occurs in the light emitting unit 16 or the first light receiving unit 18 may include a case where the condensation occurs on a light path between the light emitting unit 16 and the first light receiving unit 18 through which the light 14 passes. As an example, a case where condensation occurs in the optical filter 24 may also be included. In addition, condensation in the present example is not limited to that caused by breath, and may include condensation due to another factor, which may include contamination or the like on the light emitting unit 16 or the first light receiving unit 18.

The operating unit 20 may sense that condensation has occurred in the light path from the light emitting unit 16 to the first light receiving unit 18 based on the first light reception signal and the second light reception signal. Said light path may include the light emitting unit 16, the first light receiving unit 18, and the optical filter 24. The operating unit 20 may sense the condensation that has occurred in the light emitting unit 16 or the first light receiving unit 18 based on the variation rate ΔIR1 of the first light reception signal and the variation rate ΔIR2 of the second light reception signal. The operating unit 20 may perform operation to obtain the first light amount information described above based on the first light reception signal, and acquire the condensation determination evaluation value based on the first light amount information. The condensation determination evaluation value may be the first light amount information itself, or may be second light amount information obtained by correcting the first light amount information using the second light reception signal. The condensation determination evaluation value may be any value obtained by Expression 1 to Expression 8. The condensation determination evaluation value may be a value obtained by using the variation rate ΔIR1 of the first light reception signal and the variation rate ΔIR2 of the second light reception signal. The condensation determination evaluation value may be a ratio of the variation rate of the first light reception signal to the variation rate of the second light reception signal (ΔIR1/ΔIR2). The operating unit 20 may sense that condensation has occurred in the light path from the light emitting unit 16 to the first light receiving unit 18 based on the condensation determination evaluation value. In this manner, it can be known whether the false-positive rate of the gas sensor 10 is high. The operating unit 20 may determine that condensation has occurred when the condensation determination evaluation value is equal to or higher than 2. The above-described value may be equal to or higher than 3, or may be equal to or higher than 4. The operating unit 20 may notify the sensing result to the outside. The operating unit 20 calculates the variation amount ratio (ΔIR1/ΔIR2) by using the variation rates ΔIR1 and ΔIR2 at the same timing. The operating unit 20 may sequentially calculate the variation rate ratio (ΔIR1/ΔIR2) in time-series manner.

The operating unit 20 may determine that condensation has occurred when the variation rate of the first light reception signal is equal to or lower than a first set value. The operating unit 20 may determine that condensation has occurred when the condensation determination evaluation value is equal to or higher than the first set value. The first set value may be the variation rate of the first light reception signal or the condensation determination evaluation value when a carbon dioxide concentration of 40000 ppm is detected, as an example. The carbon dioxide concentration in human lung is said to be about 40000 ppm. When breath is released from the lung into the atmosphere, since the breath is spread into the atmosphere, carbon dioxide concentration that is equal to or greater than 40000 ppm will not be detected due to the breath. Therefore, it can be determined that condensation has occurred from the above-described first set value.

The operating unit 20 may determine that condensation has occurred in a case where the variation rate of the second light reception signal is constant and only the variation rate of the first light reception signal is reduced, as well as where the variation rate of the first light reception signal is equal to or lower than the first set value or the condensation determination evaluation value is equal to or higher than the first set value. The variation rate being constant may refer to the variation in signal values during a predetermined period being within 5%. The above-described predetermined period may be 30 seconds, may be 60 seconds, or may be a period that is ten times the breathing cycle. The operating unit 20 may determine that condensation has occurred when the difference between the variation rate of the first light reception signal and the variation rate of the second light reception signal is equal to or greater than a predetermined value. The above-described predetermined value may be a value of the variation rate of the first light reception signal (that is, the first set value) in a case where carbon dioxide concentration of 40000 ppm is detected.

Figure 3:
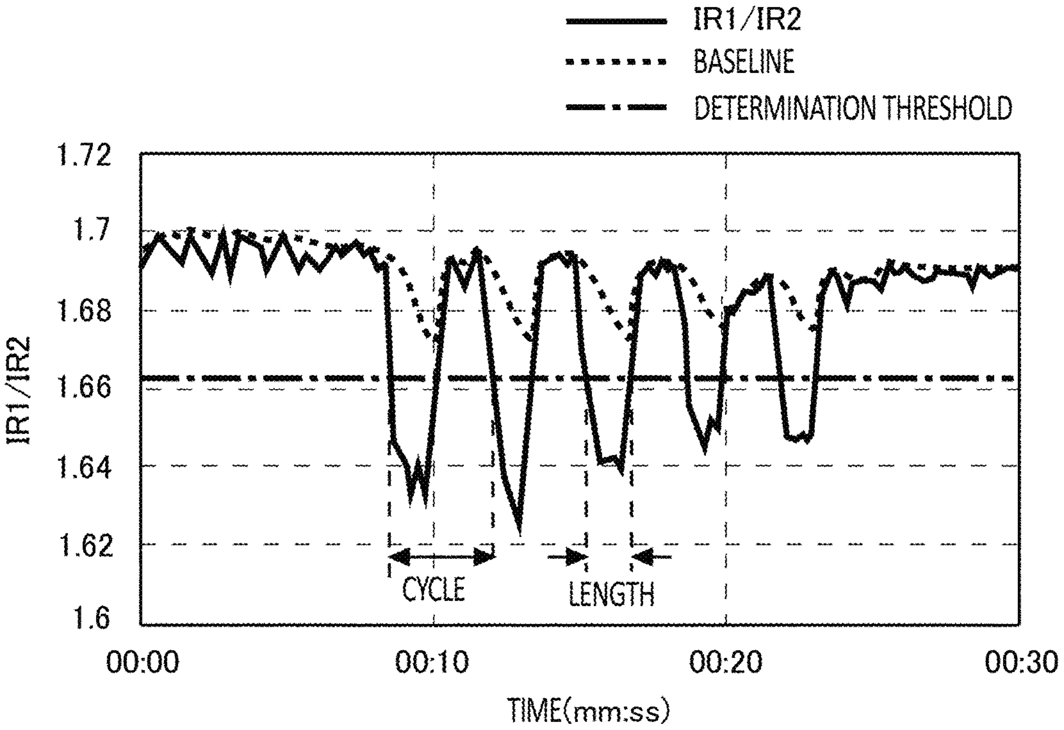
FIG. 3 illustrates calculation of a baseline.

FIG. 3 illustrates calculation of a baseline. In FIG. 3, the horizontal axis represents the time, and the vertical axis represents the value of a ratio of intensities of the first light reception signal and the second light reception signal. In the present specification, the ratio of the intensities of the first light reception signal and the second light reception signal may be referred to as the light reception signal ratio. As described above, the by dividing the first light reception signal by the second light reception signal, the output variation caused by change in the light amount of the light emitting unit 16 and temperature can be corrected. In FIG. 3, the variation in the light reception signal ratio around 10 seconds to 20 seconds corresponds to breathing. One valley-like portion in the light reception signal ratio corresponds to one breathing. In FIG. 3, since five valley-like portions appear in the waveform of the light reception signal ratio, it shows the light reception signal ratio in five breathings.

Although the embodiments are described by using the light reception signal ratio between the first light reception signal and the second light reception signal also in subsequent figures, it is not necessary to use the second light reception signal. Instead of the light reception signal ratio, signal values of the first light reception signal may be used. In this case, the term "light reception signal ratio" may be used interchangeably with the "first light reception signal". In the present specification, even in a case of performing processing on the light reception signal ratio, a similar processing may be performed on the first light reception signal, and even in a case of performing processing on the first light reception signal, a similar processing may be performed on the light reception signal ratio.

The solid lines in the figure indicates the light reception signal ratio. The one-dot chain line in the figure indicates a determination threshold described below. The operating unit 20 calculates, from the light reception signal ratio, a baseline of a waveform of the first light reception signal. The dotted line in the figure indicates the calculated baseline.

The baseline refers to a signal waveform caused by a factor (disturbance) other than the gas to be sensed. When the gas to be sensed is breath, the baseline refers to a signal waveform caused by a factor other than carbon dioxide included in the breath. The baseline is a waveform obtained by reducing or removing a component caused by the carbon dioxide concentration from the waveform shown by solid lines in FIG. 3. The baseline may include a component of the intensity of light 14 radiated by the light emitting unit 16 and a variation component caused by a factor other than a concentration change of carbon dioxide.

When the gas sensor 10 senses breath, the temperature of the light emitting unit 16 and the first light receiving unit 18 changes due to the temperature of the breath and the characteristics may change. The baseline may be a signal waveform that includes the influence of such characteristics change, but does not include the influence of carbon dioxide. The baseline caused by disturbance in which the frequency is outside the breathing cycle may include influences by moisture or degradation of elements, but in the present specification, the baseline is considered to include variation caused mainly by the temperature of breath or the temperature of breath and condensation. In the present specification, factors other than the gas to be sensed are temperature or temperature and condensation. In the subsequent description, variation caused by the temperature of the breath is described first, and subsequently, variation caused by the temperature and condensation will be described.

The operating unit 20 may calculate the baseline based on the light reception signal ratio. By doing so, the influence of the temperature caused by breath can be appropriately reflected. Even in a case where another gas to be sensed is to be sensed, if there is correlation between the disturbance and the gas to be sensed, by calculating the baseline based on the signal value of the gas to be sensed, the influence of the disturbance can be appropriately reflected.

Since the baseline calculation value in FIG. 3 is calculated from the light reception signal ratio, it is varied according to the breathing cycle, which represents the influence of the temperature caused by breath. A parameter in the baseline calculation may be experimentally decided such that the change in the light reception signal ratio caused by a factor other than carbon dioxide is represented. The parameter is a coefficient b0 described below, as an example.

The operating unit 20 may calculate the baseline by removing the frequency component of the disturbance where the frequency is offset from the breathing cycle, for the temporal waveform of the light reception signal ratio. As an example, the operating unit 20 performs calculation of the baseline by filtering represented by infinite impulse response (IIR). A process of an example of baseline calculation in IIR filtering is shown in Table 1.

TABLE 1

| | |
|---|---|
| ×0 | y0 = ×0 |
| ×1 | y1 = ×1 × b0 + y0 × (1 − b0) |
| ×2 | y2 = ×2 × b0 + y1 × (1 − b0) |
| ×3 | y3 = ×3 × b0 + y2 × (1 − b0) |

x in the table represents signal values of the light reception signal ratio, and y represents the calculated value of the baseline. b0 is a filter coefficient. The numbers following x and y represent sampling points n. In Table 1, up to n=3 is shown.

The operating unit 20 calculates the value yn of the baseline for each signal value xn of the light reception signal ratio. As shown in Table 1, the calculated value yn of the baseline is calculated as a sum of a value obtained by multiplying a corresponding signal value xn by the coefficient b0 and a value obtained by multiplying the calculated value yn−1 of the immediately preceding baseline by (1−b0). That is, the coefficient b0 decides at what percentage the value of the corresponding signal value is to be reflected to the calculated value of a prior baseline. The coefficient b0 takes a value that is equal to or higher than 0, and equal to or lower than 1. By increasing the coefficient b0, the value of the corresponding signal value is more reflected, which makes it easier for the baseline to follow the variation in the signal values. Although, in the example of Table 1, a value yn−1 of one immediately preceding baseline is reflected for the calculated value yn of the baseline, in another example, values of a plurality of immediately preceding baselines may be reflected for the calculated value yn of the baseline.

Methods like the following other than IIR filtering may be used for baseline calculation. As an example, moving average (MA) filter as shown in Expression 9 and Expression 10 may be used for the calculation.

Expression 9

$$Y_n = \frac{1}{M}\sum_{i=0}^{M-1} X_{n-i} \tag{9}$$

Expression 10

$$f_c = \frac{F_s}{2M} \tag{10}$$

Here, Yn represents the calculated value of the baseline, Xn represents the signal values, M represents a number of sections, Fs represents the sampling frequency, and fc represents the cutoff frequency.

As another example, weighted moving average (WMA) filter as shown in Expression 11 may be used for the calculation.

Expression 11

$$Y_n = \frac{\sum_{i=0}^{M-1} w_i X_{n-i}}{\sum_{i=0}^{M-1} w_i} \tag{11}$$

Here, Wi represents a weight. Other symbols are similar to those described above.

As another example, finite impulse response (FIR) filer as shown in Expression 12 and Expression 13 may be used for the calculation.

Expression 12

$$Y_n = \sum_{i=0}^{M-1} b_i X_{n-i} \tag{12}$$

Expression 13

$$f_c = \frac{F_s}{2M} \tag{13}$$

Here, bi represents the filter coefficient. Other symbols are similar to those described above.

As another example, a Butterworth filter as shown in Expression 14 may be used for the calculation.

Expression 14

$$H(s) = \frac{1}{\sqrt{1 + \left(\frac{s}{fc}\right)^{2N}}} \tag{14}$$

Here, N represents the filter order, and s represents complex frequency. Other symbols are similar to those described above.

Alternatively, in the baseline calculation, the baseline may be decided based on a value when there is less signal variation, such as data at a time when no breathing is performed. In addition, at least one value of an upper limit value or a lower limit value may be set for the baseline. In addition, a plurality of baseline calculation method may be used according to the signal value or an environmental value.

Here, an immediately preceding baseline calculation is not restricted to calculating the baseline of xn with xn−1. Any baseline calculation method may be used as long as it is difficult to follow the breathing signal. For example, for xn, baseline calculation may be performed by using all signals from xn−1 to further previous data xn-m, where m is a natural number. For example, if data has been acquired every 0.1 seconds, baseline calculation of the signal for xn may be performed by using data of signals xn−1, xn−2, xn−3, where m=3. The immediately preceding range may be decided such that it is difficult to follow the breathing signal, but can follow a slower temperature variation or the like. The calculation of the baseline may be performed based on the light reception signal ratio prior to Tn, or may be performed based on the light reception signal ratio at a particular period that is shorter than the breathing cycle prior to Tn.

The operating unit 20 removes the baseline from the light reception signal ratio. Removing the baseline may mean to subtract, from the signal value at each time, the value of the baseline at said time. By calculating and removing the baseline, the change in the signal values caused by factors other than carbon dioxide included in the breath can be corrected, allowing a more accurate measurement including sensing of condensation described above to be performed. The operating unit 20 may sense that condensation has occurred by using a signal obtained by removing the baseline from the first light reception signal, and may calculate the condensation determination evaluation value. In the present specification, the signal obtained after removing the baseline from the light reception signal ratio may be referred to as a determination signal.

The operating unit 20 may calculate at least one of the cycle or length of breathing. The operating unit 20 may calculate at least one of the cycle or length of the breathing by using the determination signal. The operating unit 20 may determine that breath is sensed when the value of the determination signal is lower than a determination threshold. The operating unit 20 may calculate the cycle or length of the breathing based on the period during which the value of the determination signal is lower than the determination threshold. The operating unit 20 may define, as the length of the breathing, one consecutive period during which the value of the determination signal is lower than the determination threshold. The operating unit 20 may calculate, as the breathing cycle, the sum of one consecutive period during which the value of the determination signal is higher than the determination threshold and one consecutive period during which the value of the determination signal is lower than the determination threshold. The operating unit 20 may calculate, as the cycle or length of the breathing, an average value within a predetermined measurement period. By calculating the cycle or length of the breathing, the emotion of the person breathing can be determined, such as whether the person is excited or relaxed. When measuring the cycle or length of the breathing, the amplitude of the determination signal does not need to be calculated and the measurement accuracy of the value of the determination signal does not need to be high, as long as the value of the determination signal and the determination threshold can be compared.

Here, setting the coefficient b0 in the infinite impulse response corresponds to removing a frequency component that is equal to or higher than a predetermined frequency from the signal value in the baseline calculation. Where said predetermined frequency is the first cut-off frequency, the relation between the first cut-off frequency and the coefficient b0 is shown in Expression 15. In Expression 15, a1=b0−1.

Expression 15

$$fc = \frac{1}{2\pi}\cos^{-1}\left(\frac{2 \times b0^2 - 1 - a1^2}{2 \times a1}\right) \tag{15}$$

The operating unit 20 may calculate the baseline based on a frequency component of a temporal waveform in the light reception signal ratio which is lower than the first cut-off frequency that is set. The baseline can be calculated based on the frequency component of the light reception signal ratio which is lower than the first cut-off frequency by setting the coefficient b0 in the infinite impulse response. Specific examples of the coefficient b0 and the first cut-off frequency will be described below.

Figure 4A:
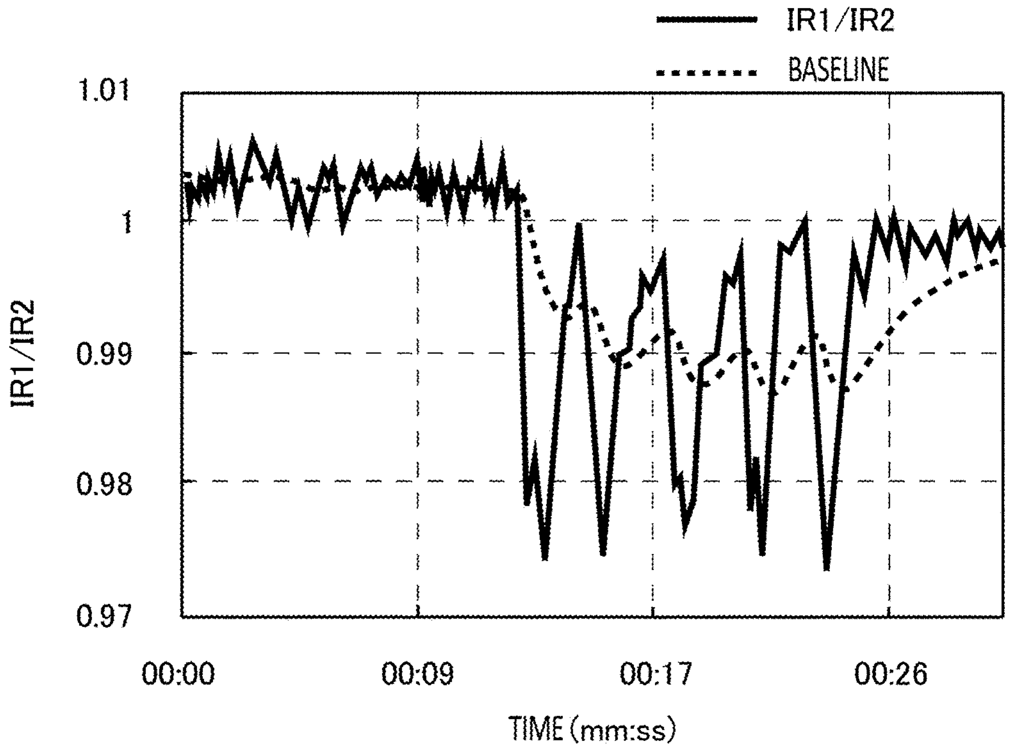
FIG. 4A illustrates a result of using a constant first cut-off frequency in the baseline calculation.

FIG. 4A illustrates a result of using a constant first cut-off frequency in the baseline calculation. The axes in FIG. 4 and solid lines and dotted lines in the figure are similar to those in FIG. 3. In the present example, the baseline calculation is performed with the first cut-off frequency being constant, for the value yn at each time in the baseline. For example, in the example of Table 1, b0 is a constant value for all n. In FIG. 4A, the followability of the baseline when the light reception signal ratio is increased is low. Thus, in a period where breathing is consecutive, the baseline does not recover to the original level (IR1/IR2=approximately 1 to 1.01), and remains at a relatively low level. In addition, immediately after the period in which breathing is consecutive ends, at some points, the baseline is lower than the light reception signal ratio.

Figure 4B:
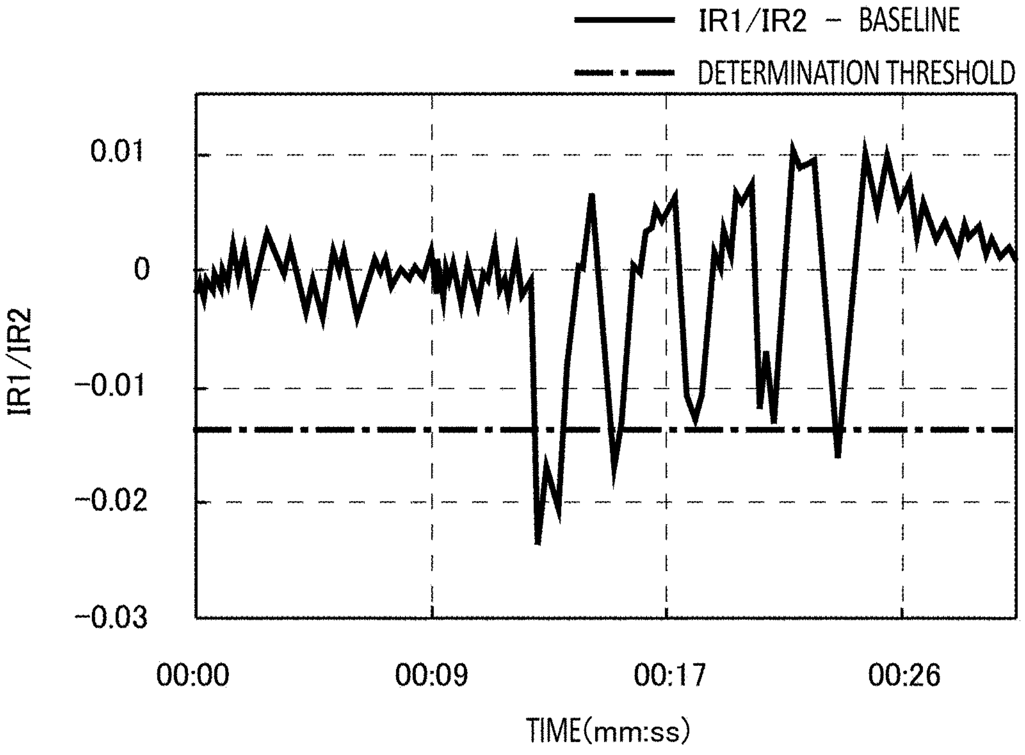
FIG. 4B illustrates a result of taking a difference between a ratio of the first light reception signal to the second light reception signal and the baseline calculation value from FIG. 4A.

FIG. 4B illustrates an example of a determination signal obtained by taking a difference between a light reception signal ratio and the baseline calculation value from FIG. 4. Since the determination signal indicates a signal component caused by breath, the determination signal in a case where no breath exists ideally matches with a reference point (IR1/IR2=0). In addition, the determination signal in a case where breath exists ideally becomes smaller than the reference point. In FIG. 4B, a part of the determination signal is positioned above (on the positive side of) the reference point (IR1/IR2=0). In other words, the determination signal is shifted upward. This is considered be because the followability of the baseline when the light reception signal ratio is increased is low, and the baseline is evaluated to be lower than the actual value.

One-dot chain lines in the figure indicate the determination threshold. As an example, it is determined that breath is sensed when the signal value is lower than the determination threshold. In FIG. 4B, only a part of the variation in the signal values caused by breath falls below the determination threshold, and a part of the breath may not be sensed. Therefore, it is preferable to more accurately calculate the breathing cycle or the like.

Figure 5A:
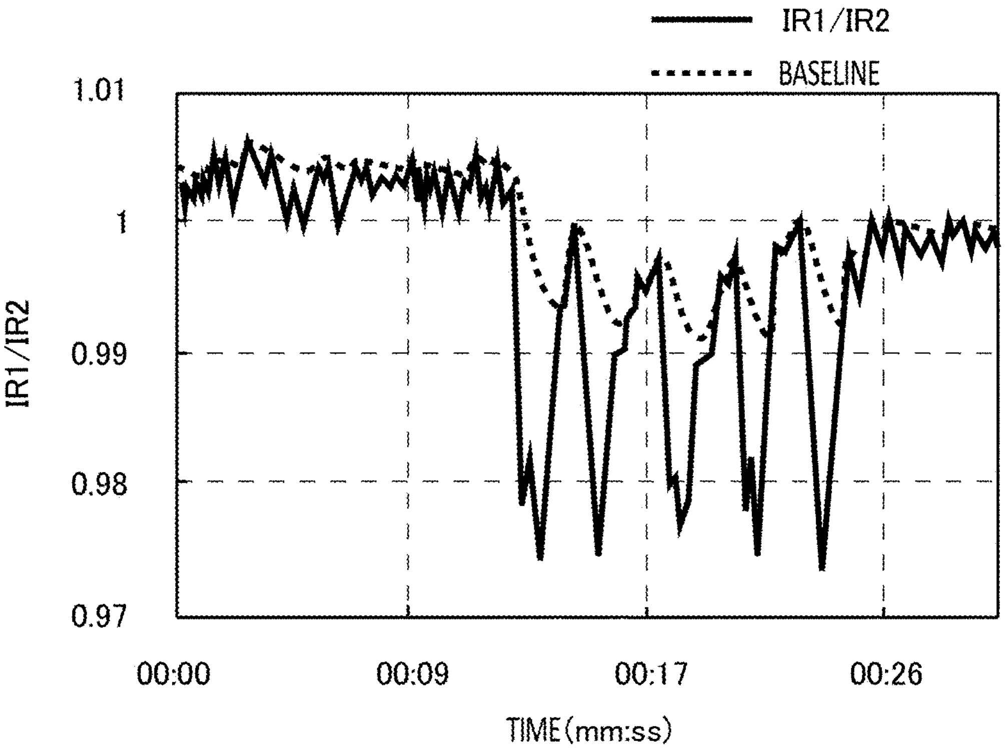
FIG. 5A illustrates a result of changing the first cut-off frequency by the magnitude relationship of an immediately preceding signal value in the baseline calculation.

FIG. 5A illustrates a result of changing the first cut-off frequency by the magnitude relationship of an immediately preceding signal value in the baseline calculation. The operating unit 20 may change the first cut-off frequency according to the change in the signal values of the light reception signal ratio. In other words, the first cut-off frequency may be set according to the change in the signal values of the light reception signal ratio. The operating unit 20 of the present example sets the first cut-off frequency in a case where the signal value of the light reception signal ratio for which the value of the baseline is to be calculated is increased relative to the signal value at an immediately preceding timing in the temporal waveform of the light reception signal ratio to be higher compared to the first cut-off frequency in a case where it is decreased relative to the immediately preceding signal value.

Using the symbols in Table 1, the first cut-off frequency in a case where $xn>xn-1$ is set to be higher compared to the first cut-off frequency in a case where $xn<xn-1$. The operating unit 20 may set the coefficient b0 in a case where $xn>xn-1$ to be greater than the coefficient b0 in a case where $xn<xn-1$ to set the first cut-off frequency to be higher. By setting the first cut-off frequency to be higher, a relatively high frequency component in the signal waveform of the first light emitting signal can be reflected to the baseline. Thus, followability of the baseline when the signal value of the first light emitting signal is increased is improved. In FIG. 5A, the baseline closely follows the increase in the signal value of the first light emitting signal. Thus, the baseline returns near the original value (1 to 1.01), as compared to the example in FIG. 4A, in the period during which breathing is consecutive and the period immediately after.

In addition, in a case where the breath flows into the gas sensor 10, after the carbon dioxide is sensed, the temperature of an element is increased due to the temperature of the breath. Thus, it can be considered that an influence on the temperature characteristic of the element will appear in the temporal waveform of the baseline. Since the temperature of the element changes in synchronism with the breathing, the valley portion that is synchronous with the breathing as shown in FIG. 5A appears in the temporal waveform of the baseline. The influence of the temperature of the breath is considered to appear later than the sensing of carbon dioxide. By setting the first cut-off frequency as described above, in a period during which the signal value of the light reception signal ratio is reduced, the baseline calculation value is less likely to follow the variation in the signal values caused by sensing of carbon dioxide, which allows the baseline calculation value to be less influenced by carbon dioxide to appropriately reflect the influence of the temperature of the breath.

The operating unit 20 may set the first cut-off frequency in a case where the signal value of the light reception signal ratio for which the value of the baseline is to be calculated is increased relative to the signal value at a past timing in the temporal waveform of the light reception signal ratio to be higher compared to the first cut-off frequency in a case where it is decreased relative to the past signal value. The above-described past signal value may be an average value of the light reception signal ratio in a period that is shorter than the breathing cycle, which ends at the immediately preceding light reception signal ratio, may be the signal value of any light reception signal ratio in said period, or may be the signal value of all of the light reception signal ratios in said period. Using the symbols in Table 1, as an example, the first cut-off frequency in a case where xn is higher than the average value of $xn-1$, $xn-2$, and $xn-3$ may be set to be higher compared to the first cut-off frequency in a case where xn is lower than said average value.

Figure 5B:
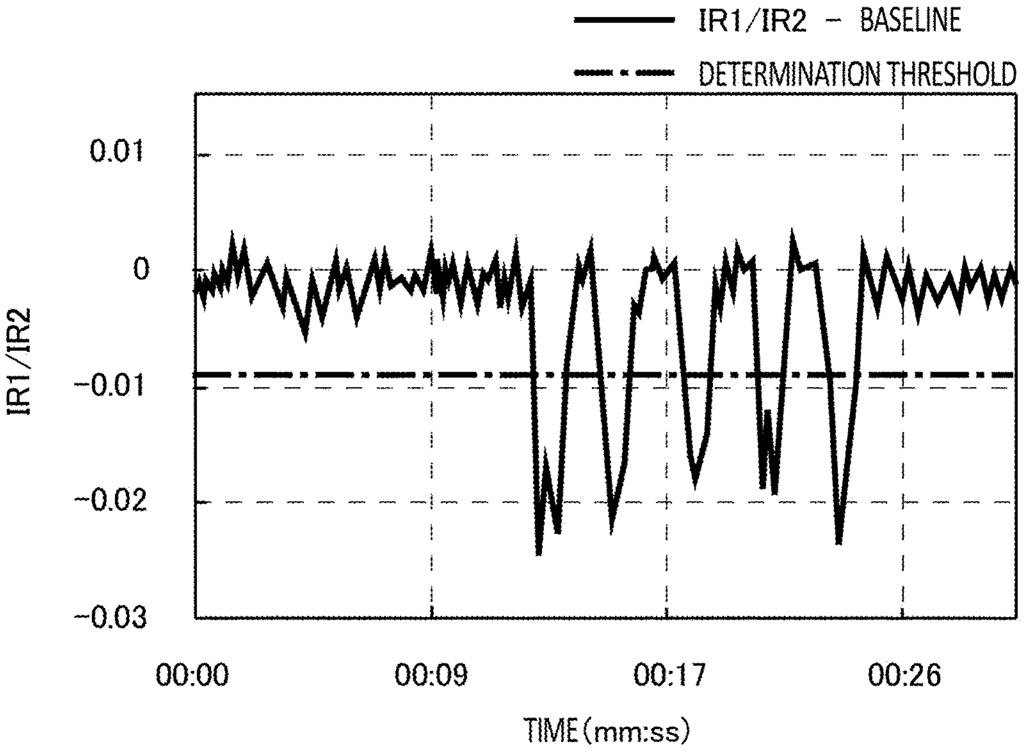
FIG. 5B illustrates a determination signal calculated from a light reception signal ratio and the baseline illustrated in FIG. 5A.

FIG. 5B illustrates a determination signal calculated from a light reception signal ratio and the baseline illustrated in FIG. 5A. In FIG. 5B, other than minute noise components, the determination signals at all times are positioned below the reference point (IR1/IR2=0). Similarly to that in FIG. 4B, the one-dot chain line in the figure indicates the determination threshold. According to the present example, shifting of the determination signal can be suppressed, which allows breathing to be sensed and the cycle of length of the breathing to be calculated more accurately.

The operating unit 20 may set the first cut-off frequency in a case where the signal value of the light reception signal ratio for which the value of the baseline is to be calculated is increased relative to the signal value at an immediately preceding timing in the temporal waveform of the light reception signal ratio to be higher by ten times or more compared to the first cut-off frequency in a case where it is decreased relative to the immediately preceding signal value. As an example, the first cut-off frequency in a case where $xn>xn-1$ may be set to be equal to or higher than 1 Hz (for example, about 1.8 Hz (coefficient b0=0.24)), and the first cut-off frequency in a case where $xn<xn-1$ may be set to be equal to or lower than 0.1 Hz (for example, about 0.06 Hz (coefficient b0=0.01)). In this manner, the followability of the baseline is more improved. The above-described scale factor may be two times or more, may be five times or more, or may be 20 times or more. The first cut-off frequency may be equal to or lower than 3 Hz. Note that, the signal value at the above-described immediately preceding timing may be the past signal value described above.

Figure 6A:
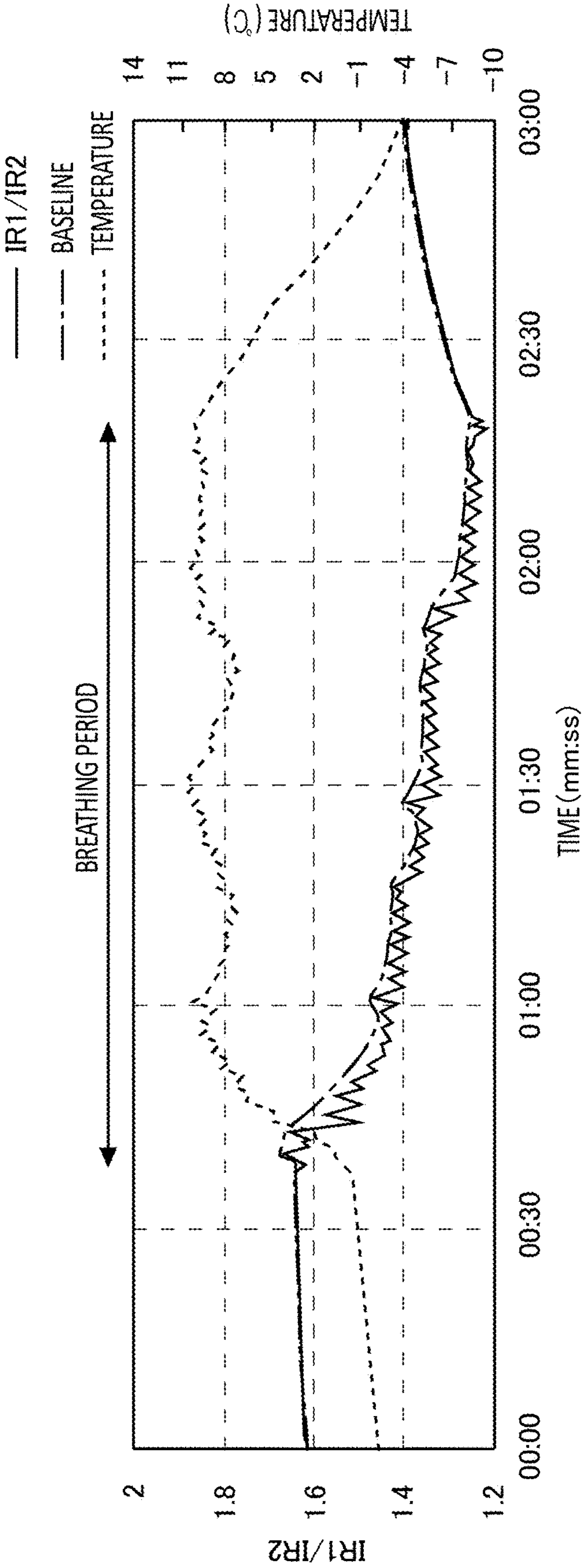
FIG. 6A illustrates a baseline calculation in a case where condensation has occurred.

FIG. 6A illustrates a baseline calculation in a case where condensation has occurred. In FIG. 6A, the horizontal axis represents time, the vertical axis on the left-hand side represents the light reception signal ratio, and the vertical axis on the right-hand side represents the temperature. The solid lines in the figure represent the light reception signal ratio, the one-dot chain line in the figure represents the baseline, and the dotted line in the figure represents the temperature of the gas sensor 10.

In FIG. 6A, similarly to FIG. 2, breath is blown onto the gas sensor 10 at about 0° C. Breathing is performed from 40 seconds to 2 minutes and 20 seconds in the figure, and the gas sensor 10 senses the breath during the above-described period. The above-described period is shown as the breathing period in the figure. Minute variation in the light reception signal ratio during the breathing period corresponds to the breathing. One valley-like portion in the light reception signal ratio corresponds to one breathing. In FIG. 6A, breathing is performed approximately 40 times during the breathing period.

Also in the present example, breath is blown onto the gas sensor 10 at about 0° C., and condensation is purposely caused to occur. In FIG. 6A, the light reception signal ratio is significantly reduced at around 40 seconds, and subsequently continues to be reduced until 2 minutes and 20 seconds where the breathing ends. This reduction in the light reception signal ratio is considered to be influenced by the condensation caused by breath.

In FIG. 6A, the operating unit 20 calculates the baseline. The calculation method is the IIR filtering described above. In the present example, the baseline calculation is performed with the first cut-off frequency being constant, for the value yn at each time in the baseline.

In FIG. 6A, since condensation has occurred, the light reception signal ratio during the breathing period continues to decrease. Therefore, there are some points where the baseline during the breathing period is unable to follow the decrease in the light reception signal ratio. Particularly, it is unable to follow the decrease in the light reception signal ratio at the initial stage (40 seconds to 1 minute) during the breathing period where the decrease in the light reception signal ratio caused by occurrence of the condensation is large.

Figure 6B:
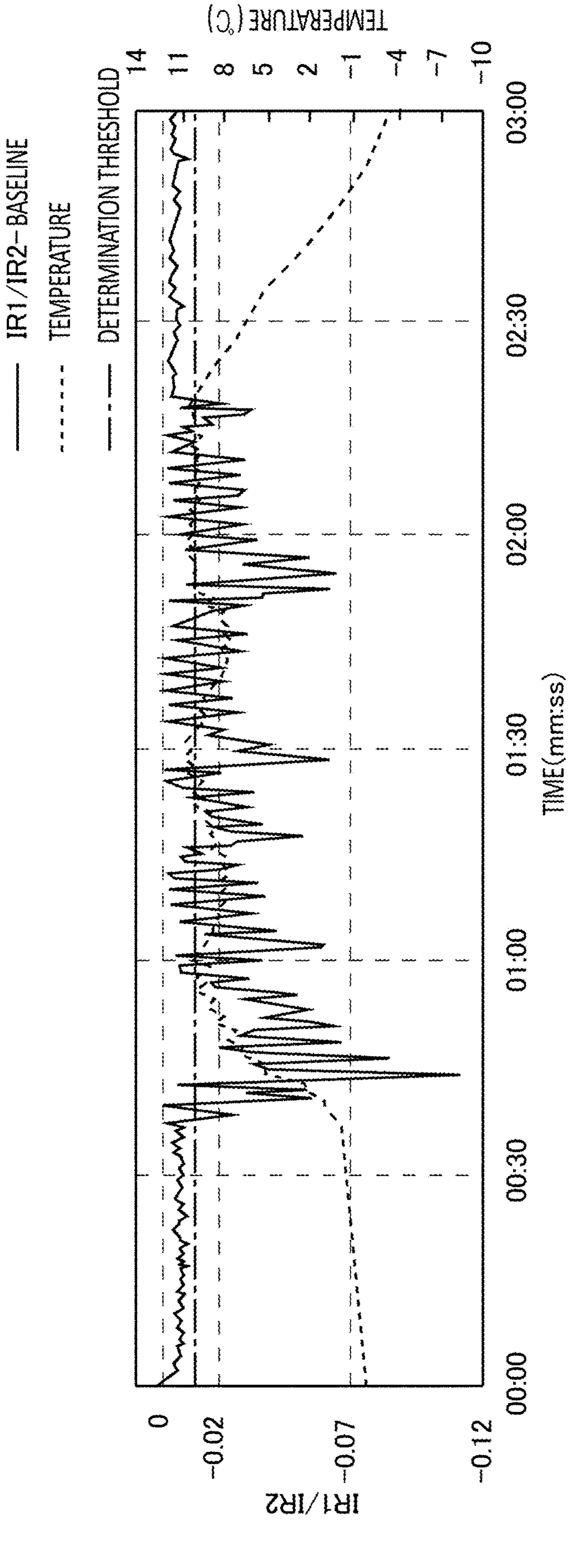
FIG. 6B illustrates an example of a determination signal obtained by taking the difference between the light reception signal ratio and the baseline calculation value in FIG. 6A.

FIG. 6B illustrates an example of a determination signal obtained by taking the difference between the light reception signal ratio and the baseline calculation value in FIG. 6A. Since the determination signal indicates a signal component caused by breath, the determination signal in a case where no breath exists ideally matches with a reference point (IR1/IR2=0). Also when breath exists, since carbon dioxide spreads between breathings (the mountain portion between valley portions), the determination signal in a case were no breath exists ideally matches with the reference point (IR1/IR2=0). However, in FIG. 6B, many mountain portions are positioned below (on the negative side of) the reference point. This is considered to be because the variation in the signal values caused by condensation is unable to be appropriately reflected to the baseline. A larger number of the mountain portions positioned below (on the negative side) is particularly observed in the initial stage (40 seconds to 1 minute) during the breathing period.

One-dot chain lines in the figure indicate the determination threshold. As an example, the it is determined that breath is sensed when the signal value is lower than the determination threshold. In FIG. 6B, only a part of the variation in the light reception signal ratio caused by breath crosses the determination threshold, and other variations are positioned below (on the negative side of) the determination threshold. In this case, since it is determined that the period in which the light reception signal ratio is positioned below (on the negative side of) the determination threshold is in the course of one breathing, it may lead to misdetection of the cycle and length of the breathing. Therefore, it is preferable to calculate the baseline more accurately.

Figure 7A:
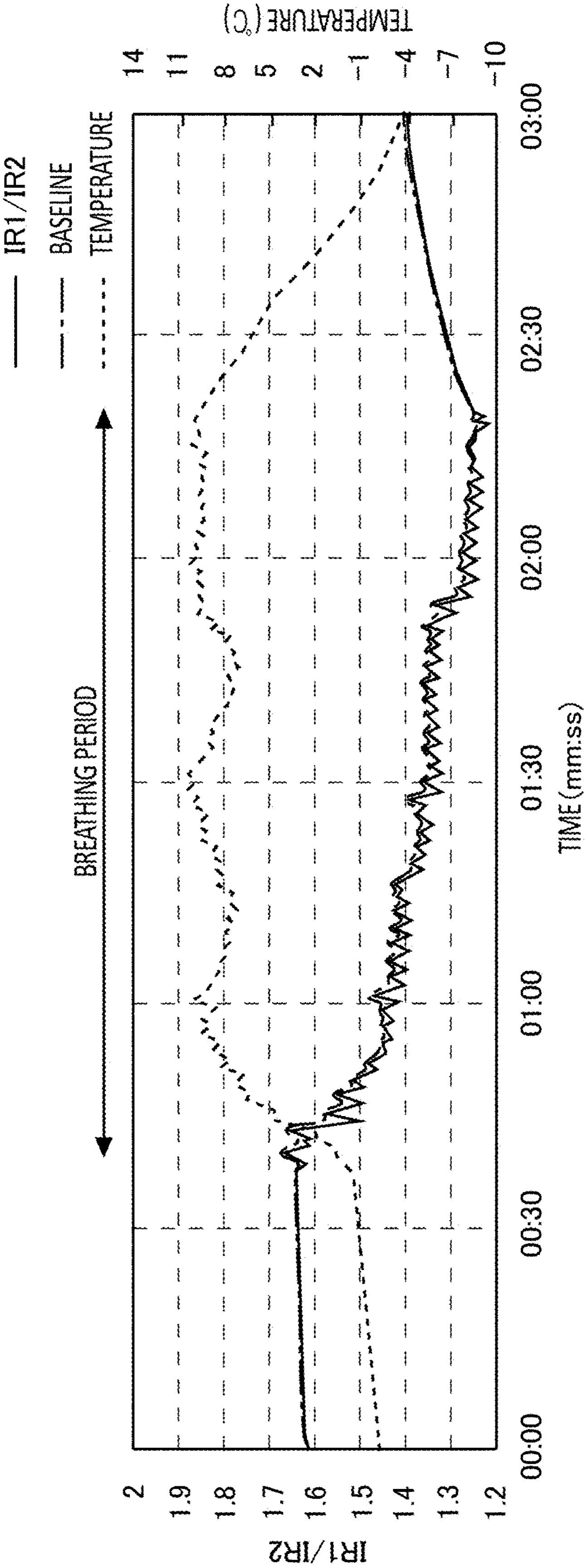
FIG. 7A illustrates a result of changing the first cut-off frequency in the baseline calculation in a case where condensation has occurred.

FIG. 7A illustrates a result of changing the first cut-off frequency in the baseline calculation in a case where condensation has occurred. Each axis and each line in FIG. 7A are similar to those in FIG. 6A. The operating unit 20 may change the first cut-off frequency at the time when condensation is sensed. The operating unit 20 may set the first cut-off frequency at the time when condensation is sensed to be higher than the first cut-off frequency when no condensation is sensed. In this manner, it becomes easier for the baseline to follow the variation in the light reception signal ratio caused by the condensation. In other words, the influence of the condensation can be appropriately included in the baseline. Sensing of the condensation may be performed by the method described in FIG. 2. In addition, components other than the cutoff frequency, such as the attenuation trend, the filter order, and the type of the low pass filter may be changed.

Figure 7B:
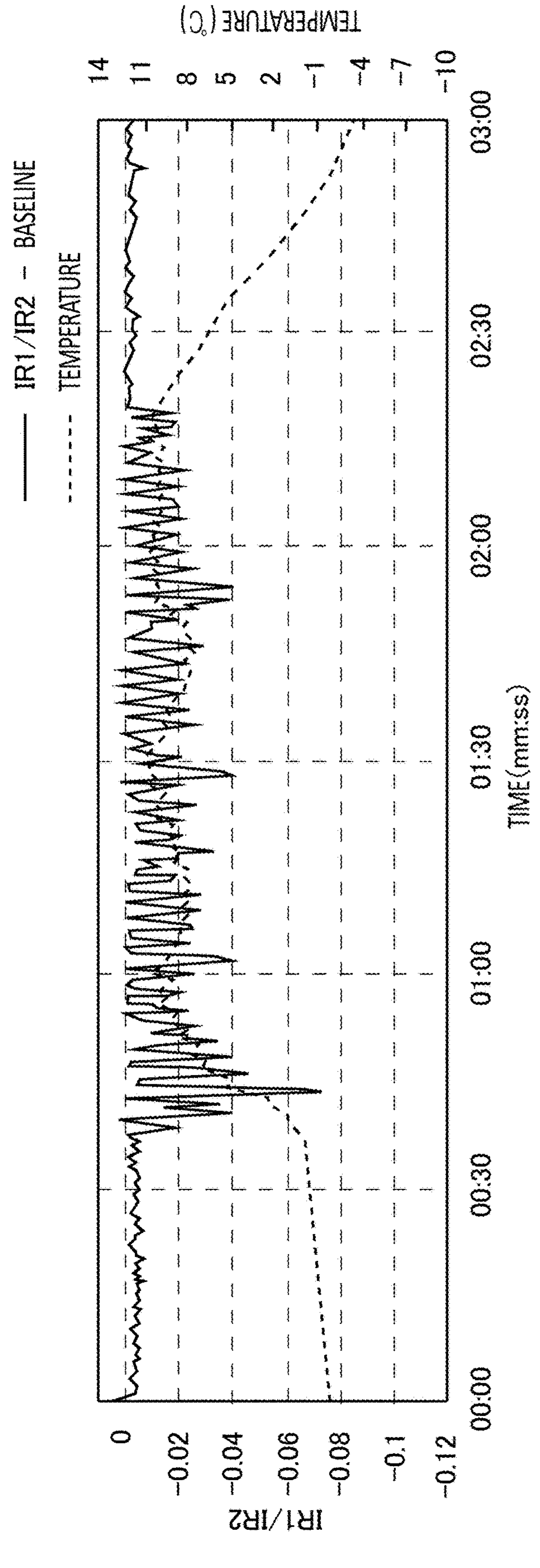
FIG. 7B illustrates an example of the determination signal calculated from the light reception signal ratio and the baseline calculation value in FIG. 7A.

FIG. 7B illustrates an example of the determination signal calculated from the light reception signal ratio and the baseline calculation value in FIG. 7A. In FIG. 7B, the portions between breathings (the mountain portions between valley portions) generally match with the reference point (IR1/IR2=0). That is, the influence of condensation can be appropriately corrected for. Note that, in FIG. 7B, illustration of the determination threshold is omitted. Decrease in the light reception signal ratio caused by the condensation is particularly large at the initial stage (from 40 seconds to 1 minute in FIG. 6A and FIG. 7A) during the breathing period. When the signal value of the light reception signal ratio for which the value of the baseline is to be calculated is decreased by a second set value or more relative to the signal value at an immediately preceding timing in the temporal waveform of the light reception signal ratio, the operating unit 20 may set the first cut-off frequency to be higher compared to the first cut-off frequency when condensation is sensed. In this manner, the followability of the baseline can be improved also at the initial stage during the breathing period where the variation is particularly large.

As described above, the carbon dioxide concentration in the lung is approximately 40000 ppm. When flowing into the gas sensor 10 from the lung as breath, the carbon dioxide spreads into the atmosphere, so the concentration sensed by the gas sensor 10 is considered to be approximately 10000 ppm. The second set value may be a signal value in a case where carbon dioxide concentration of 20000 ppm or 30000 ppm is detected, as an example.

The operating unit 20 may determine whether the condensation is caused by breath based on the variation in the light reception signal ratio or the signal value of the baseline. When the condensation is caused by breath, the decrease in the light reception signal ratio at the initial stage during the breathing period is larger compared to when the condensation is caused by other factors. Therefore, the operating unit 20 may determine that condensation has occurred due to breath, when the decrease amount in the light reception signal ratio or the baseline within a predetermined time from the beginning of the breathing period is equal to or greater than a predetermined value. Said predetermined time may be an average value of the breathing cycle, and may be 10 seconds, 20 seconds, or 30 seconds. Said predetermined value may be the variation amount of the signal value in a case where a carbon dioxide concentration of 20000 ppm, 30000 ppm, or 40000 ppm is detected.

The operating unit 20 may determine whether the condensation is caused by breath based on the ratio of an absolute value of the gradient of the baseline from the beginning of the breathing period until a predetermined time elapses and an absolute value of the gradient of the baseline from the end of the breathing period until a predetermined time period elapses. As described above, in a case where the condensation is caused by breath, the absolute value of the gradient of the baseline immediately after the beginning of the breathing period becomes relatively large. The operating unit 20 may determine that condensation has occurred due to breath in a case where a value obtained by dividing the absolute value of the gradient of the baseline at a predetermined period after beginning of the breathing period by the absolute value of the gradient of the baseline at a predetermined period after the end of the breathing period is equal to or greater than the predetermined value.

Figure 8:
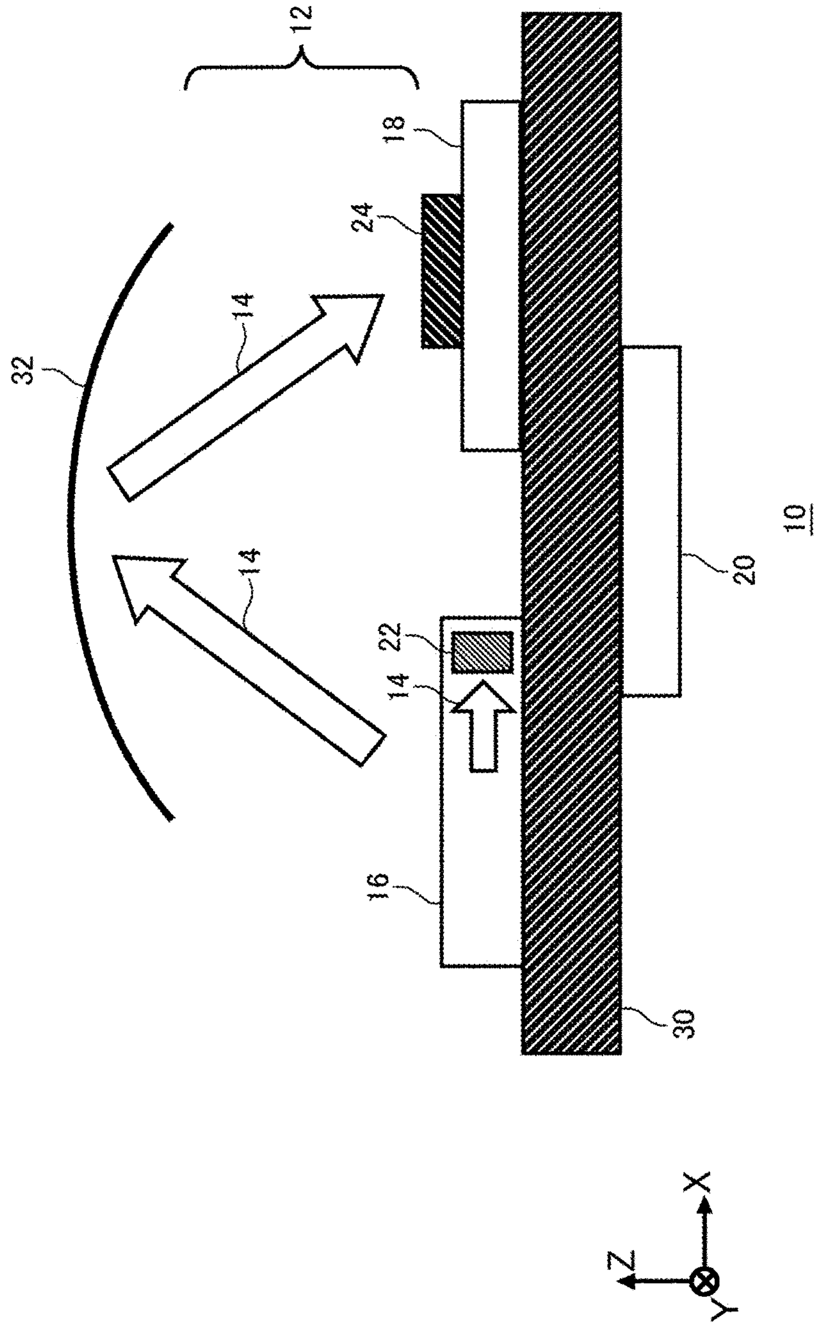
FIG. 8 illustrates another embodiment of the gas sensor 10.

FIG. 8 illustrates another embodiment of the gas sensor 10. The gas sensor 10 of the present example has the light emitting unit 16, the first light receiving unit 18, and the operating unit 20 attached to the same support member 30. The gas sensor 10 of the present example includes a mirror 32, and the area between the support member 30 and the mirror 32 becomes the path 12 through which the gas to be sensed passes. In the gas sensor 10 of the present example, a part of the light 14 radiated by the light emitting unit 16 is reflected by the mirror 32, and the first light receiving unit 18 receives the reflected light 14. Other portions may be similar to those of the gas sensor 10 in FIG. 1. By taking such a configuration, the gas sensor 10 can be made in a compact manner.

Figure 9:
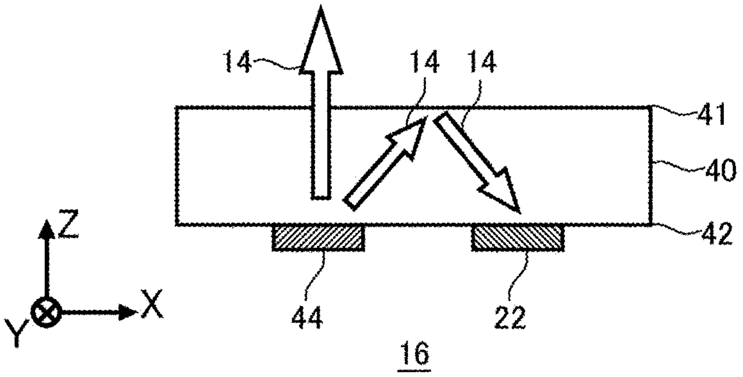
FIG. 9 illustrates a configuration example of the light emitting unit 16.

FIG. 9 illustrates a configuration example of the light emitting unit 16. The light emitting unit 16 of the present example includes a substrate 40, a light emitting element 44, and a second light receiving unit 22. The substrate 40 may be transparent to the light 14. When breath is to be sensed, the substrate 40 is a GaAs substrate, as an example.

The substrate 40 includes a first main surface 41 and a second main surface 42. The first main surface 41 and the second main surface 42 are two main surfaces that constitute the substrate 40. In the present example, of the two main surfaces, the first main surface 41 is the main surface on the positive side in the Z-axis direction, and the second main surface 42 is the main surface on the negative side in the Z-axis direction. The first main surface 41 faces the path 12 through which the gas to be sensed passes.

The light emitting element 44 and the second light receiving unit 22 may be provided on the same substrate. The light emitting element 44 and the second light receiving unit 22 of the present example are provided on the second main surface 42 of the substrate 40. The light emitting element 44 includes a laminated structure unit of PN junction or PIN junction. By supplying electrical power to this laminated structure unit, the light emitting element 44 operates as LED, and emits the light 14 with a wavelength according to the band gap of the material of the laminated structure unit. When breath is to be sensed, the light emitting element 44 may use, as the laminated structure unit, InAlSb that can perform an output near an absorption wavelength of carbon dioxide. The light emitting element 44 described above is referred to as a quantum infrared light emitting element.

A part of the light 14 proceeds through the substrate 40, passes through the first main surface 41, and is released to the path 12. On the other hand, other parts of the light 14 proceeds through the substrate 40, is reflected on the first main surface 41, and enters the second light receiving unit 22.

The second light receiving unit 22 receives the light 14 that proceeded through the substrate 40. In other words, the second light receiving unit 22 receives the light 14 that did not pass through the path 12 (a space where the gas to be sensed exists) through which the gas to be sensed passes. In this manner, the output variation caused by the change in the light amount of the light emitting element 44 and temperature can be corrected. The second light receiving unit 22 may receive only the light 14 that did not pass through the space where the gas to be sensed exists.

The second light receiving unit 22 may also include a laminated structure unit. The laminated structure unit of the second light receiving unit 22 may be a diode structure of PN junction or PIN junction. The laminated structure unit and the material of the second light receiving unit 22 may be similar to the laminated structure unit and the material of the light emitting element 44. In this manner, the temperature characteristic of the second light receiving unit 22 and the temperature characteristic of the light emitting element 44 can be matched with each other. The second light receiving unit 22 described above is referred to as a quantum infrared light receiving element.

Figure 10:
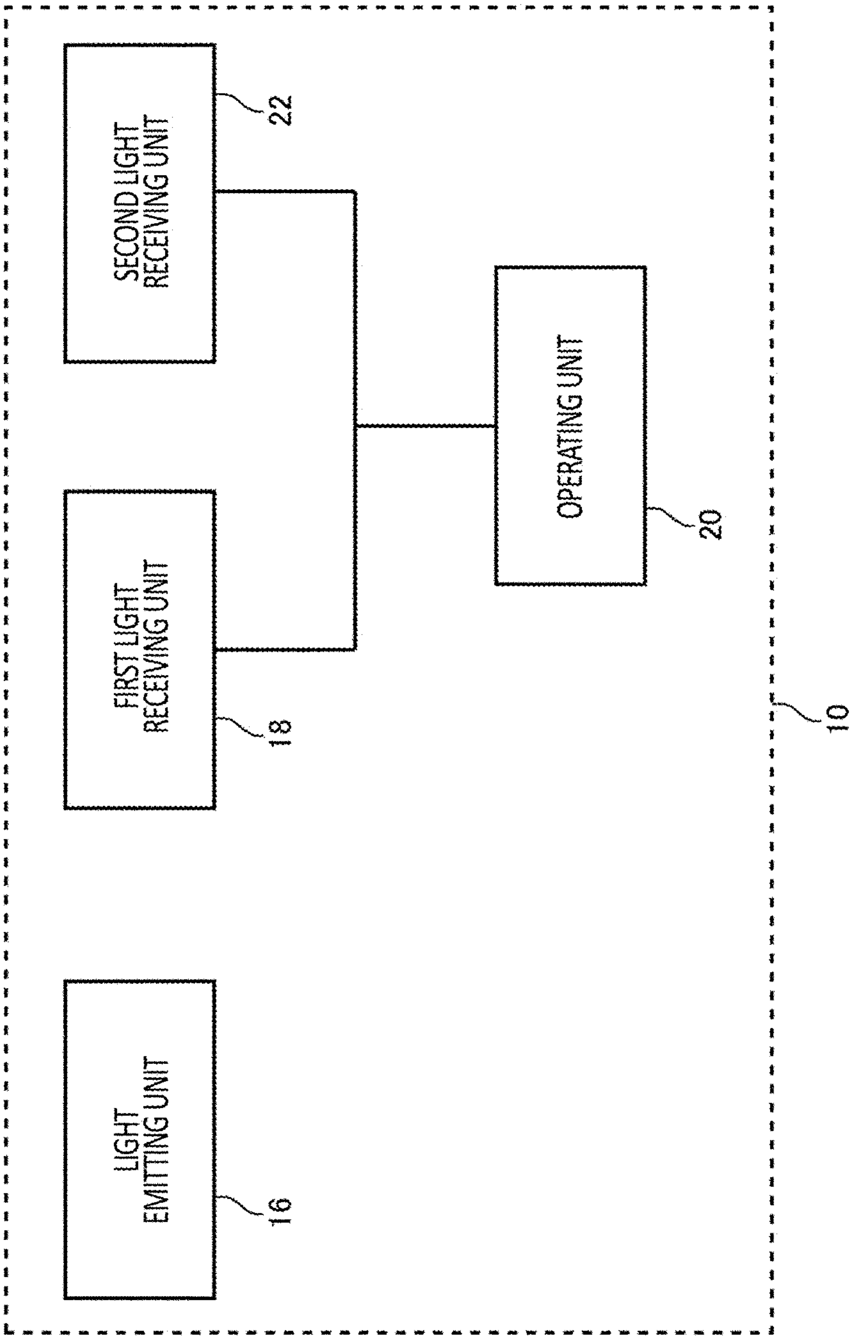
FIG. 10 illustrates an example block diagram of the gas sensor 10 in the example.

FIG. 10 illustrates an example block diagram of the gas sensor 10 in the example. In FIG. 10, the light emitting unit 16, the first light receiving unit 18, the second light receiving unit 22, and the operating unit 20 of the gas sensor 10 are illustrated.

As described above, the first light receiving unit 18 receives at least a part of the light 14 that is radiated from the light emitting unit 16 and that passed through the gas to be sensed. The first light receiving unit 18 outputs a first light reception signal according to the light reception result to the operating unit 20.

As described above, the second light receiving unit 22 receives at least a part of the light 14 that is radiated from the light emitting unit 16 and that did not pass through the gas to be sensed. The second light receiving unit 22 outputs a second light reception signal according to the light reception result to the operating unit 20.

The operating unit 20 acquires the first light reception signal from the first light receiving unit 18, and acquires the second light reception signal from the second light receiving unit 22. As described above, the operating unit 20 senses that condensation has occurred in the light path from the light emitting unit 16 to the first light receiving unit 18 based on the first light reception signal and the second light reception signal. The operating unit 20 may sense the condensation through various methods described above. In addition, the operating unit 20 may perform calculation and removal of the baseline described above. The operating unit 20 may calculate the cycle or length of the breathing described above.

Figure 11:
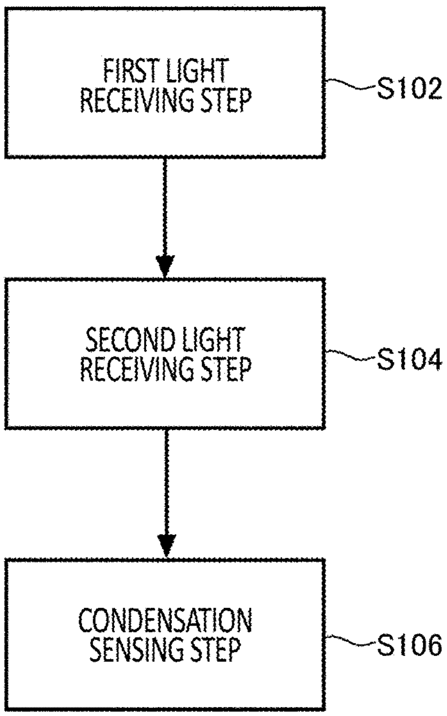
FIG. 11 illustrates an example flowchart of a sensing method.

FIG. 11 illustrates an example flowchart of a sensing method. The sensing method of the present example includes a first light receiving step S102, a second light receiving step S104, and a condensation sensing step S106. At the first light receiving step S102, at least a part of the light 14 that is radiated to the path 12 through which the gas to be sensed passes and that passed through the gas to be sensed is received, and a first light reception signal according to the light reception result is output. The first light receiving step S102 is performed by the first light receiving unit 18 described above.

At the second light receiving step S104, at least a part of the light 14 that did not pass through the gas to be sensed is received, and a second light reception signal according to the light reception result is output. The light 14 may be light that did not pass through the path 12. The second light receiving step S104 is performed by the second light receiving unit 22 described above. In FIG. 11, the second light receiving step S104 is performed after the first light receiving step S102, but the order may be reversed, or the two steps may be performed at the same time.

At the condensation sensing step S106, it is sensed that condensation has occurred in the light path through which the light 14 passes based on the first light reception signal and the second light reception signal. The condensation sensing step S106 is performed by the operating unit 20 described above. At the condensation sensing step S106, condensation may be sensed through various methods including the condensation determination evaluation value or the like described above. In addition, at the condensation sensing step S106, calculation and removal of the baseline described above may be performed. At the condensation sensing step S106, the cycle or length of the breathing described above may be calculated.

While the present invention has been described by way of the embodiments, the technical scope of the present invention is not limited to the above-described embodiments. It is apparent to persons skilled in the art that various alterations or improvements can be made to the above-described embodiments. It is also apparent from the described scope of the claims that the embodiments added with such alterations or improvements can be included the technical scope of the present invention.

What is claimed is:

1. A gas sensor that senses gas to be sensed, comprising
a light emitting unit that radiates light;
a first light receiving unit that receives at least a part of the light that passed through the gas to be sensed, and outputs a first light reception signal according to a light reception result;
a second light receiving unit that receives at least a part of the light that did not pass through the gas to be sensed, and outputs a second light reception signal according to a light reception result; and
an operating unit that senses that condensation has occurred in a light path from the light emitting unit to the first light receiving unit based on the first light reception signal and the second light reception signal, wherein
the light emitting unit includes a substrate, a light emitting element, and the second light receiving unit,
the substrate includes a first main surface and a second main surface,
the light emitting element, and the second light receiving unit are provided on the second main surface of the substrate,
a part of the light emitted from the light emitting element proceeds through the substrate,
the first light receiving unit receives a part of the light that passes through the first main surface, and
the second light receiving unit receives the at least a part of the light that was reflected on the first main surface, and did not pass through the gas to be sensed.

2. The gas sensor according to claim 1, wherein
the operating unit calculates a variation rate of the first light reception signal and a variation rate of the second light reception signal, and
determines that the condensation has occurred based on a condensation determination evaluation value obtained by using the variation rate of the first light reception signal and the variation rate of the second light reception signal.

3. The gas sensor according to claim 2, wherein
the operating unit calculates a baseline of a waveform of the first light reception signal based on a frequency component of the first light reception signal that is lower than a first cut-off frequency that is set, and senses that the condensation has occurred based on a signal obtained by removing the baseline from the first light reception signal.

4. The gas sensor according to claim 3, wherein
the condensation determination evaluation value is a ratio of the variation rate of the first light reception signal to the variation rate of the second light reception signal, and
the operating unit determines that the condensation has occurred when the ratio is equal to or higher than a first set value.

5. The gas sensor according to claim 3, wherein
the first cut-off frequency is set according to a change in signal values of the first light reception signal, and
the operating unit sets the first cut-off frequency in a case where the signal value of a light reception signal ratio for which the value of the baseline is to be calculated is increased relative to the signal value at a past timing in the temporal waveform of the light reception signal ratio to be higher compared to the first cut-off frequency in a case where it is decreased relative to the past signal value.

6. The gas sensor according to claim 3, wherein
the operating unit sets the first cut-off frequency at a time when the condensation is sensed to be higher than the first cut-off frequency when no condensation is sensed.

7. The gas sensor according to claim 6, wherein
the operating unit calculates at least one of a cycle or a length of breathing including the gas to be sensed by using the signal obtained by removing the baseline from the first light reception signal.

8. The gas sensor according to claim 3, wherein
the operating unit determines that the condensation has occurred based on the variation rate of the first light reception signal or the condensation determination evaluation value when a carbon dioxide concentration included in a breath is detected.

9. The gas sensor according to claim 8, wherein
whether the condensation has occurred or not is made based on the variation rate of the first light reception signal or the condensation determination evaluation value relative to a first set value, and
the first set value is a value when the carbon dioxide concentration included in the breath is detected.

10. The gas sensor according to claim 3, wherein
the operating unit determines that the condensation has occurred when the variation rate of the second light reception signal is constant and the variation rate of the first light reception signal is reduced.

11. The gas sensor according to claim 10, wherein
the variation rate being constant refers to a variation in signal values during a predetermined period being within 5%, and
the predetermined period is 30 seconds.

12. The gas sensor according to claim 4, wherein
the operating unit calculates the baseline from time-series information of a light reception signal ratio between the first light reception signal and the second light reception signal and determines that the condensation has occurred using a determination signal obtained after removing the baseline from the light reception signal ratio and a ratio of a variation rate to the determination signal.

13. The gas sensor according to claim 12, wherein
the first set value is set based on the ratio of the variation rate of the first light reception signal to the variation rate of the second light reception signal when a carbon dioxide concentration included in a beath is detected.

14. The gas sensor according to claim 12, wherein
the operating unit determines that the condensation has occurred when the variation rate of the second light reception signal is constant and the variation rate of the first light reception signal is reduced.

15. The gas sensor according to claim 14, wherein
the variation rate being constant refers to a variation in signal values during a predetermined period being within 5%, and
the predetermined period is 30 seconds.

16. The gas sensor according to claim 12, wherein the operating unit calculates at least one of a cycle or a length of breathing including the gas to be sensed by using the signal obtained by removing the baseline from the first light reception signal.

17. The gas sensor according to claim 16, wherein the operating unit calculates a baseline calculation value based on a baseline calculation method different from that used for the state in which condensation does not occur by changing the first cut-off frequency when the condensation has occurred, and calculates the at least one of the cycle or the length of breathing from the baseline calculation value and the determination signal calculated from the light reception signal ratio.

18. The gas sensor according to claim 1, further comprising: a thermometer, wherein the operating unit receives temperature information from the thermometer, and the operating unit corrects, in an operation on the first light reception signal, first light amount information of the first light reception signal using second light amount information of the second light reception signal with the following formula including the temperature information;

$$\Phi 2comp \propto \frac{f_1(Temp)\int \Phi_1(\lambda, Temp)Ri_1(\lambda, Temp)\left(1 - e^{-c\mu(\lambda,Temp)L}\right)d\lambda}{f_2(Temp)\int \Phi_2(\lambda, Temp)Ri_2(\lambda, Temp)d\lambda}$$

Φ1: the first light amount information,
Φ2: the second light amount information,
λ: wavelength,
$\Phi_1(\lambda)$: an intensity of the light, among the light emitted from the light emitting unit, that reached the first light receiving unit in a case where a sensing gas does not exist,
$\Phi_2(\lambda)$: an intensity of the light that reached the second light receiving unit,
$Ri_1(\lambda)$: responsivity of the first light receiving unit,
$Ri_2(\lambda)$: responsivity of the second light receiving unit,
L: an optical path length from the light emitting unit to the first light receiving unit,
μ(λ): an absorption light coefficient of sensing gas
c: concentration of gas to be sensed
f1: temperature corrected expression of a signal of the light reception sensor
f2: temperature corrected expression of a signal of the second light receiving unit
Φ2comp: value of Φ2 after temperature correction.

* * * * *